United States Patent [19]

Rau

[11] Patent Number: 5,505,729
[45] Date of Patent: Apr. 9, 1996

[54] PROCESS AND AN ARRANGEMENT FOR HIGH-PRESSURE LIQUID CUTTING

[75] Inventor: Horst-Günter Rau, München, Germany

[73] Assignee: Dornier Medizintechnik GmbH, Germany

[21] Appl. No.: 5,209

[22] Filed: Jan. 15, 1993

[30] Foreign Application Priority Data

Jan. 16, 1992 [DE] Germany .............................. 9200452 U

[51] Int. Cl.⁶ ..................................................... A61B 17/39
[52] U.S. Cl. .................................. 606/40; 606/49; 604/22
[58] Field of Search .......................... 604/20–22; 606/49, 606/50, 159, 166–167; 239/706, DIG. 8; 417/395

[56] References Cited

U.S. PATENT DOCUMENTS

| | | | |
|---|---|---|---|
| 2,888,928 | 6/1957 | Seiger | 606/49 |
| 3,818,913 | 6/1974 | Wallach | 606/166 |
| 4,741,678 | 5/1988 | Nehring | 417/395 |
| 4,878,493 | 11/1989 | Pasternak et al. | 606/50 |
| 4,913,698 | 4/1990 | Ito et al. | 604/22 |
| 4,931,047 | 6/1990 | Broadwin et al. | 604/22 |
| 5,037,431 | 8/1991 | Summers et al. | |
| 5,135,482 | 8/1992 | Neracher | 606/159 |
| 5,370,609 | 12/1994 | Drasler et al. | 604/22 |

FOREIGN PATENT DOCUMENTS

| | | | |
|---|---|---|---|
| 2051068 | 3/1992 | Canada | 604/22 |
| 0258901A2 | 3/1988 | European Pat. Off. . | |
| 0280972A1 | 9/1988 | European Pat. Off. . | |
| 280972 | 9/1988 | European Pat. Off. | 606/50 |
| 0411170A1 | 2/1991 | European Pat. Off. . | |
| 225618A1 | 8/1985 | German Dem. Rep. . | |
| 234608A1 | 4/1986 | German Dem. Rep. . | |
| 8814873.4 | 11/1988 | Germany . | |

OTHER PUBLICATIONS

"Resection of the liver with a Water Jet" Br. J. Surg. vol. 69 (1982) 93–94.

Primary Examiner—C. Fred Rosenbaum
Assistant Examiner—Mark Bockelman
Attorney, Agent, or Firm—Evenson, McKeown, Edwards & Lenahan

[57] ABSTRACT

A process and apparatus for high-pressure liquid cutting of organic tissue in which a high-frequency electric signal is superimposed on the liquid cutting jet so that, while the cutting effect is selective, an additional coagulation of small vessels is possible.

9 Claims, 6 Drawing Sheets

PROCESS AND AN ARRANGEMENT FOR HIGH-PRESSURE LIQUID CUTTING

This invention relates to a process and apparatus for high-pressure liquid cutting of organic tissue, particularly for the severing of parenchymal tissue.

Today's hepatectomy procedures are based on dividing the liver into different lobes and segments according to the branchings of the afferent blood vessels in the region of the portal field, as well as according to the localization of the efferent hepatic veins. During the resection of liver metastases, and in the case of primary tumors in the liver, it is important to remove the tumor in a manner that is as parenchyma-saving as possible in the healthy surroundings. The following significant problems must be solved in this case:

1. The resection must minimize the loss of blood;
2. The duration of the resection should be as short as possible;
3. The afferent blood vessels (hepatic artery and portal vein) must be clamped as briefly as possible (or not at all) in order to minimize or eliminate the thermal ischemia time, which is damaging to the organ; and
4. The afferent and efferent vessels and hepatic ducts of segments that follow must not be damaged during resection of central segments.

In the finger fraction technique used heretofore, the parenchyma is crushed between the fingers in order to isolate and ligate the larger vessels (Pachter 1983); thus, this procedure does not meet the above requirements. For this reason, more and more technical devices are used in hepatic surgery. In addition to thermal procedures, such as the laser and the high-frequency electrocauterizer (which cannot discriminate between parenchyma and vascular structure, and is therefore rarely used today), the ultrasonic aspirator has gained in importance (Hodgson 1979, 1984; Scheele 1989). In this device, a metal tube, which is provided with a suction arrangement, is set into axial vibration by means of ultrasound. Because of differing tissue resistances, this technique permits selective cutting, that is, a severing of the vessels from the parenchyma. While the overall view is good, the more resistant vessels can then be individually gripped and tied, so that the loss of blood can be reduced. However, since the cutting speed is slow, this procedure takes longer than the finger fracture technique.

In the jet cutting technique, a liquid is pressurized by a high-pressure pump and is conducted by a high-pressure pipe to a nozzle, where the pressure is converted to kinetic energy. The relationship between the liquid pressure p and the exit speed of the liquid jet v is as follows:

$$v = \mu * \sqrt{p/q}$$

where q is the viscosity of the liquid. The losses which occur during the energy conversion are determined essentially by the outflow number $\mu$, which is a function of the nozzle geometry. Thus, this outflow number is a measure of the relationship between the actually and theoretically achievable jet speed.

The development of a divergent liquid jet in air was described by YANAIDA 1980: In the core zone, there is a compact turbulent liquid jet which disintegrates with increasing distance, into individual liquid bundles and then into drops. In the continuous Jet range, the axial speed remains almost constant; in the drop-shaped range, it decreases until it falls abruptly in the dissolution range.

For jet cutting of parenchymal tissue, pressure values of from 10 to 50 bar, with nozzles with diameters of from 0.05 to 0.2 mm, were found to be useful (Bengmark 1987; Papachristou 1982; Une 1989; Rau 1990), because within these parameters the softer liver parenchyma is washed off the harder vessels and hepatic ducts, so that these structures are clearly shown, and (as in the case of the ultrasonic aspirator) can be gripped separately and tied (Bengmark 1987; Papachristou 1982; Une 1989). The advantage of this technique is a significantly higher cutting speed, while the cutting quality remains the same (Rau 1989, 1990). In addition, this technique permits no-contact working, is simple, and is less expensive than the ultrasonic aspirator technique.

In the field of coagulation, an argon beam of Erbe Co. is known, in which an argon gas is ionized by way of a high frequency, and this energy can be transmitted to the tissue for the purpose of coagulation. However, cutting is not possible by means of this technique.

The application of a high frequency to no-contact coagulation using an NaCl solution as a conduction transmitter has also been described (Reidenbach, 1988). However, this process is used only for preventing a gluing-together of the conventional metal electrodes with the tissue to be coagulated; the selective cutting effect of a high-pressure jet is not taken into account. This leads to significant differences.

European Patent Document EP 280 972 A1, discloses a liquid jet cutting arrangement having an instrument holder which comprises a coagulation electrode in addition to the cutting nozzle from which the cutting jet emerges. This arrangement is used only to simplify handling during the change from cutting to coagulating during the surgery. Cutting and coagulating take place in a staggered manner with respect to time and independently of one another according to respective known methods.

The above described jet cutting instruments (Bengmark, Une, Papachristou, Beer) use reciprocating pump systems, which do not permit a complete separation of the cutting solution from the pump system.

In the meantime, the jet cutting technique has been used clinically, and the empirical knowledge gained in experiments can be confirmed (Bengmark 1987; Papachristou 1982, Une 1989, Rau 1990). Nevertheless, all possibilities of this technique have not been exhausted.

It is an object of the present invention to provide a cutting instrument which yields an improved cutting speed and quality compared to known prior art devices. This object is achieved according to the invention, in which the known jet cutting technique is combined with high-frequency coagulation, with an electric high frequency superimposed on the liquid cutting jet. As a result, while the cutting effect is selective, an additional coagulation of small vessels is possible, and a cut with almost no bleeding is achieved. The important advantages of the combination of these two techniques include enhanced cutting speed and a reduction of the loss of blood, thus minimizing the stress experienced by the patient.

The prerequisite for the implementation of the combination according to the invention of jet cutting and high-frequency coagulation is the complete electric and hygienic separation of the cutting liquid from the pressure generating device. For this reason, the development of special pressure generating devices was required.

So that an electric high frequency can be impressed on the cutting jet, an electrically conductive liquid must be used as the cutting liquid. Preferably, a physiological electrolyte solution or a hyperosmotic solution is used. Advantageously, an admixture is added to the cutting liquid, which lowers the surface tension in order to thus increase the exit speed.

In an advantageous embodiment, the cutting liquid is heated before it emerges from the nozzle, which can also increase the surface tension. Furthermore, by means of the heating, when suitable parameters are selected for the formation of the liquid jet, a thermal coagulation can already be achieved or the coagulation effect of the high frequency superimposed on the cutting jet can be further increased.

With the use of a 5–20% NaCl solution, a working pressure of 10–100 bar, a nozzle cross-section of 0.05–0.2 mm, a high frequency in a range of from 100–1,000 kHz and a voltage $U_{eff}$ of above 1,200 volt (preferably between 1,200 nd 3,000 volt), the cutting jet develops the following characteristics: In the dissolution range of the jet (approximately 5 mm beyond the exit from the nozzle), a yellowish spark will ignite to the tissue to be cut. A cut with sharp incision edges, coagulated small capillaries and preserved larger vessels is thus provided. The cut surface is also dry with respect to blood. This process results in an improvement of parenchymal surgery and opens up possibilities of expanded surgical intervention in the liver, the pancreas, the spleen, the kidneys, etc.

Other objects, advantages and novel features of the present invention will become apparent from the following detailed description of the invention when considered in conjunction with the accompanying drawings.

DETAILED DESCRIPTION OF THE DRAWINGS

All pressure generating systems described hereinbelow are electrically and hygienically completely separated from the cutting solution. Only in this manner is it possible to connect a high-frequency coagulator whose energy is transmitted to the tissue to be cut by way of the fine liquid jet (preferred parameters: nozzle size 0.05 to 0.2 mm; pressure 10 to 100 bar). For this purpose, an electrically conductive liquid is to be used (such as 5–20% NaCl). In the case of a high frequency of 300 kHz and a voltage of 1,000 volt, the transmission of power levels of up to 120 watts have been achieved in experiments.

Figure 1:
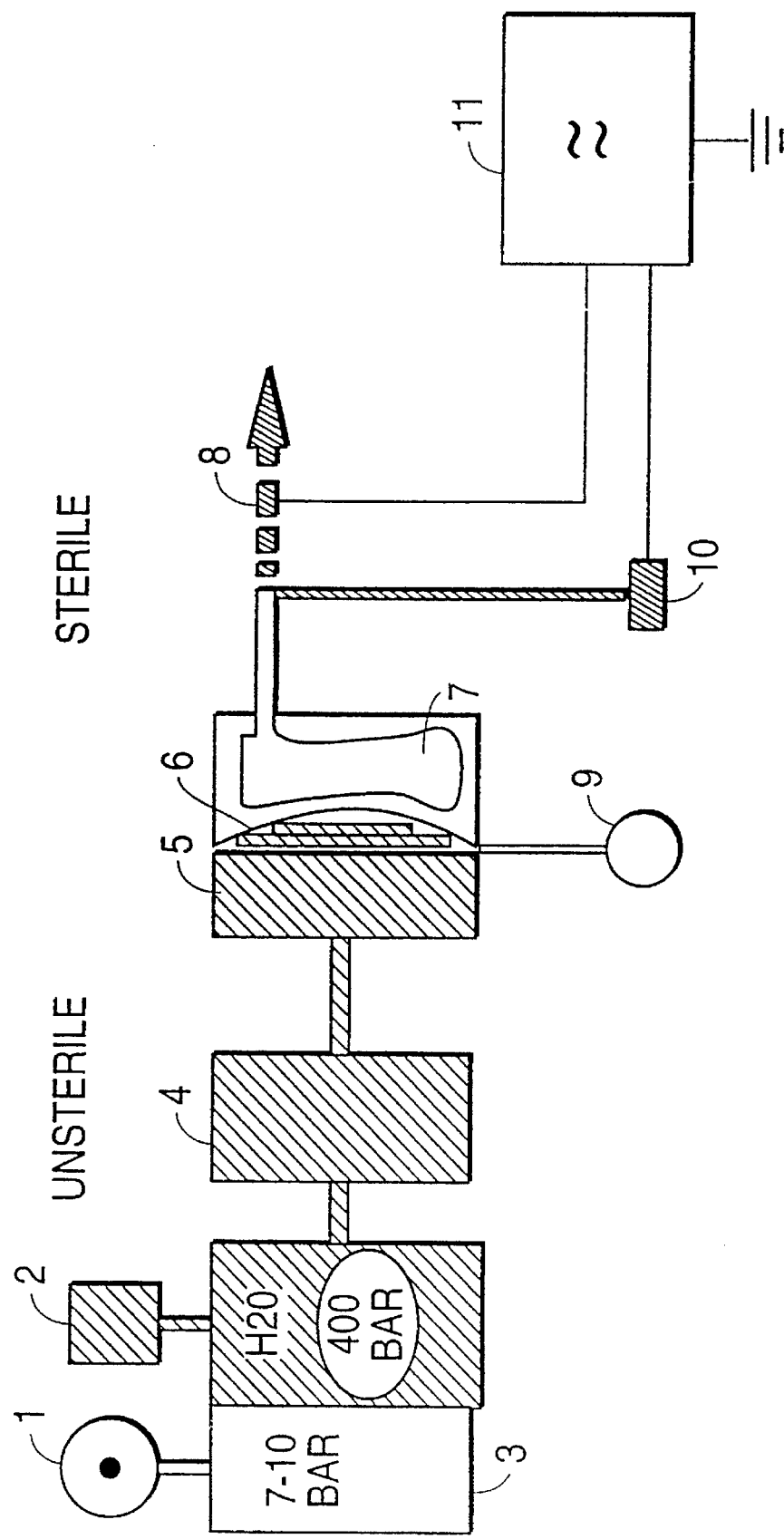
FIGS. 1 to 4 illustrate various advantageous embodiments of the arrangement according to the invention.

Referring to FIG. 1, pressure is generated by way of a compressed-air operated high-pressure pump 3, which is driven with an air pressure of from 7 to 10 bar by way of an air pressure connection 1, and generates up to 500 bar of pressure on an unsterile liquid, such as $H_2O$, provided by reservoir 2. A pressure compensation tank 4 transmits the pressure into a pressure chamber 5, which has a pressure gauge 9 and a separating membrane 6 that transmits the pressure to a liquid which is then used for cutting as a high-pressure liquid jet 8, by way of a nozzle mounted on an instrument holder. The cutting solution is contained in commercially available infusion pouches 7 installed in the pressure chamber 5 in an electrically insulated manner. As a result, two separate working circuits are available, each being closed to the pressurized cutting liquid, and kept sterile in itself. This permits sterile working during an operation, with the additional application of an electric high frequency by way of the jet. An electric high-frequency generator 11, which advantageously has a current limiting device, provides a high-frequency electric signal to the instrument holder with the nozzle 8. The high-frequency signal is switched on by means of the foot-actuated switch 10. However, it is also possible to replace the foot-actuated switch by an on/off switch which is mounted directly on the instrument holder. By means of the described arrangement, a pressure of up to 500 bar can be generated.

Figure 2:
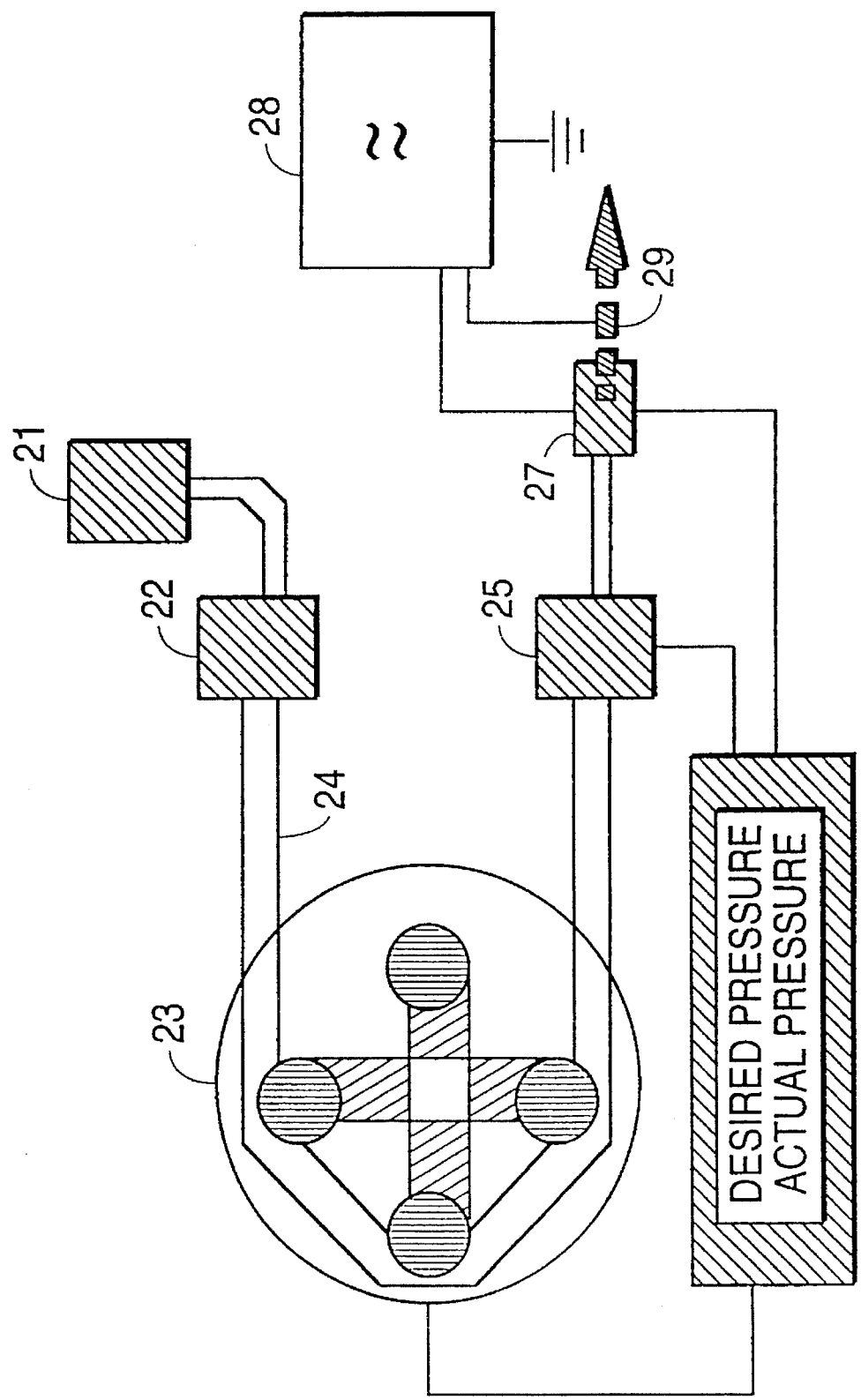
Figure 3:
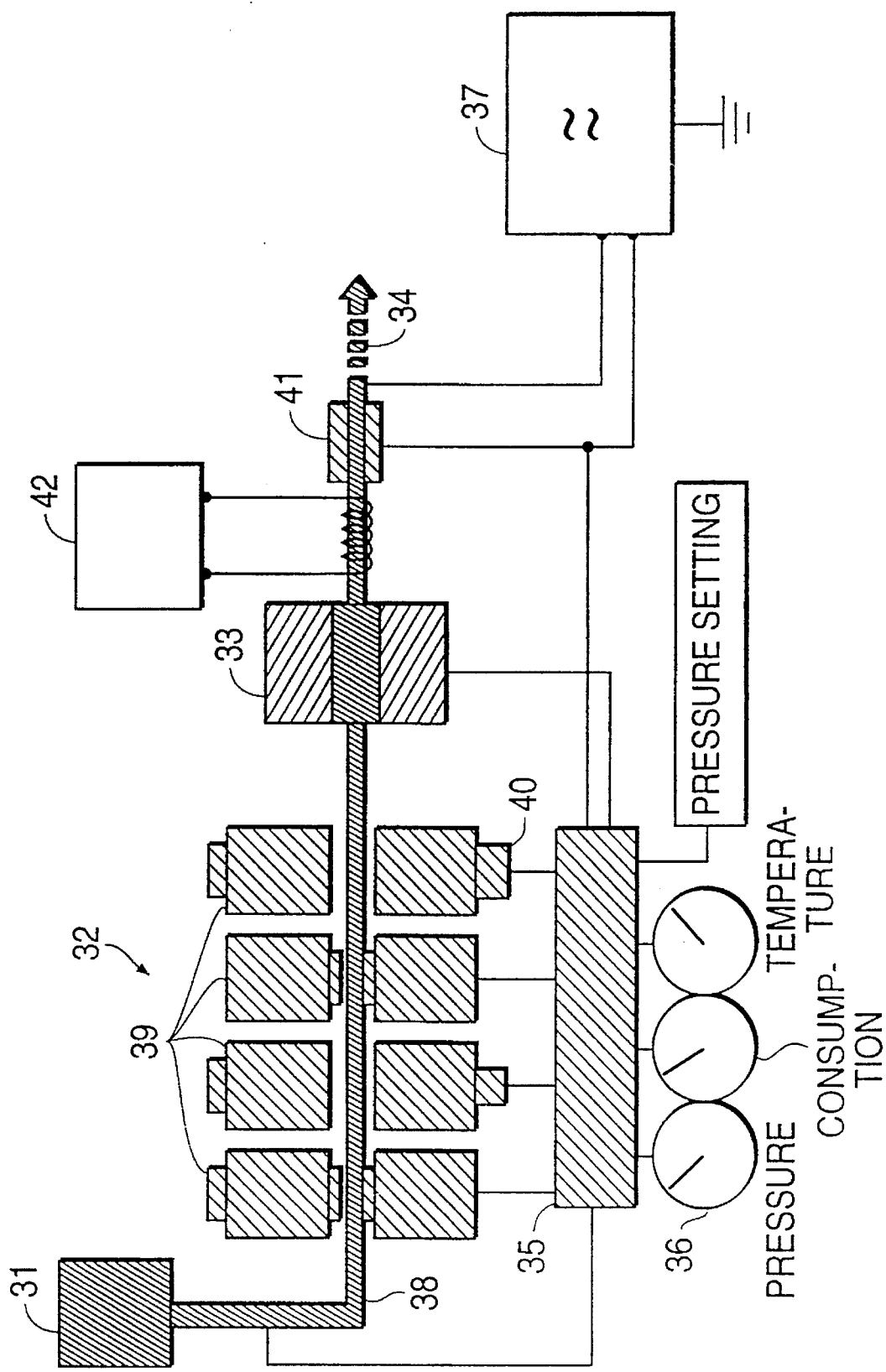
Figure 4:
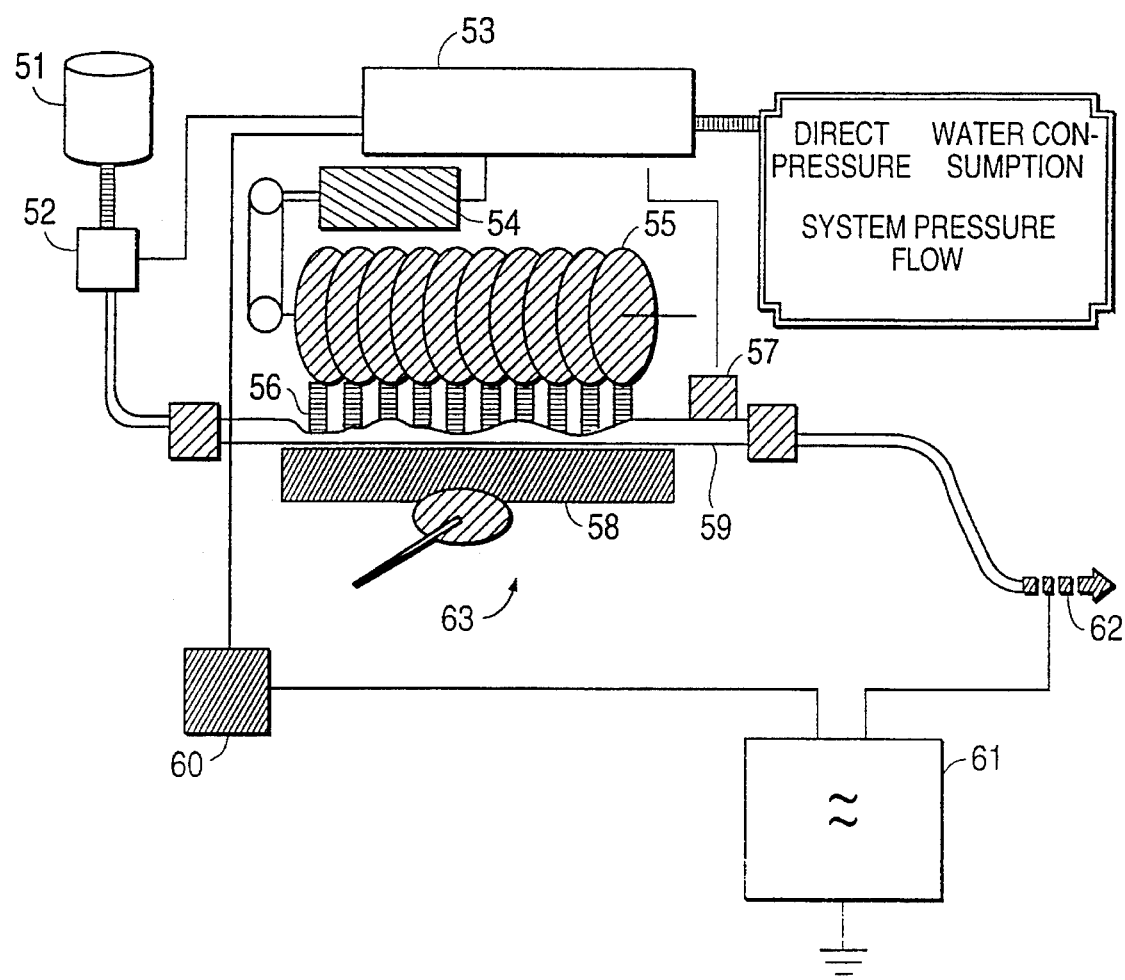

Additional advantageous embodiments of the invention, which are illustrated in FIGS. 2 to 4, are obtained by the use of a peristaltic pump for generating pressure within the cutting liquid. A peristaltic pump generally comprises a flexible pressure hose, in which the medium to be acted upon is disposed, as well as devices (such as pump fingers) which generate pressure by pressing on the hose. In each of the arrangements according to FIGS. 2 to 4, the cutting liquid is guided from a storage tank, through the pressure hose of the peristaltic pump, to the nozzle.

For lower pressures of up to maximally 100 bar, a simplified arrangement for generating pressure by means of a peristaltic pump, such as a roller pump as shown in FIG. 2, is sufficient. From a storage tank 21, the jet solution is fed by way of the high-pressure hose 24 supported by holder 22, into the roller pump 23, to the nozzle on the instrument holder 29. The working pressure within the jet solution is detected by a pressure sensor 25, such as a strain gauge or a pressure gauge, and fed to a computer 26 which controls the pump to achieve a predetermined desired pressure. The high frequency signal of the high frequency generator 28 is connected at a switch 27 which is arranged directly on the instrument holder 29.

Here also, the high-pressure technology is completely separate from the sterile jet solution. In this embodiment, the exchange of the used-up jet solution is simpler because no pressure chamber must be opened, and thus cutting does not have to be interrupted.

In the embodiment of FIG. 3, in order to maintain the separation of sterile jet solution from the generation of pressure, and at the same time to be able to control the air dome effect occurring in the pressure hose 18, a linear peristaltic pump 32 is used, in which individually controllable pump fingers 40, driven by step motors 39, are pressed against the high-pressure hose 38 to apply pressure to the sterile jet solution from reservoir 31. The step motors 39 are activated by means of an electronic control device 35, which controls the output pressure of pump 32 in response to pressure information from sensor 33 in the same manner as the embodiment of FIG. 2. (Temperature, pressure and consumption data are displayed on the monitor 36.) Controlling the generation of pressure in this manner also permits pulsed-mode operation.

The air dome effect has the result that, after the pump 32 is switched off, the water jet stops only after a delay. By means of this linear peristaltic pump, however, several pump fingers 40 can be set back simultaneously, so that an immediate stoppage of the jet can be achieved. The high-frequency current of the generator 37 is connected by way of a switch on the instrument holder 34. As an alternative, a foot-actuated switch may also be used. By means of the heater 42, the temperature of the cutting liquid may be increased. For this purpose, it is connected with a heating element and a heat exchanger which are mounted on the high-pressure hose 38 in the area between the pump 32 and the nozzle 34.

As in the case of the arrangement according to FIG. 3, the pressure generating device in FIG. 4 is a linear pump 63, in which the jet solution provided from reservoir 51 via meter 52 is guided to the nozzle 62 by a high-pressure hose 59. A worm gear 55 is driven by a motor 54 and presses pump fingers 56 sequentially against the pressure hose 59, which is supported on contact pressure rail 58. The pump 63 is controlled electronically by a computer 53 in response to pressure information from sensor 57, to provide a preselectable working pressure. The residual pressure which, according to the air dome principle, will still be present in the hose system after switch off of the pump, is relieved by way of a pump return. Connection of the high-frequency signal of the generator 61 as well as the working pressure of the jet solution are controlled by way of a foot-actuated switch 60. As an alternative, a manual switch on the instrument holder may also be used.

In the case of all described pump systems, the jet solution is electrically isolated from the pressure generating medium, which permits connection of high-frequency energy from a high-frequency coagulator. In order also to keep the high-frequency leakage current through the pressure hose to the pressure generating device as low as possible, it is advantageous to use a choke, which is wound with the pressure hose, or to use other HF filters. Another solution is keeping the lumen of the pressure hose as small as possible.

Figure 5A:
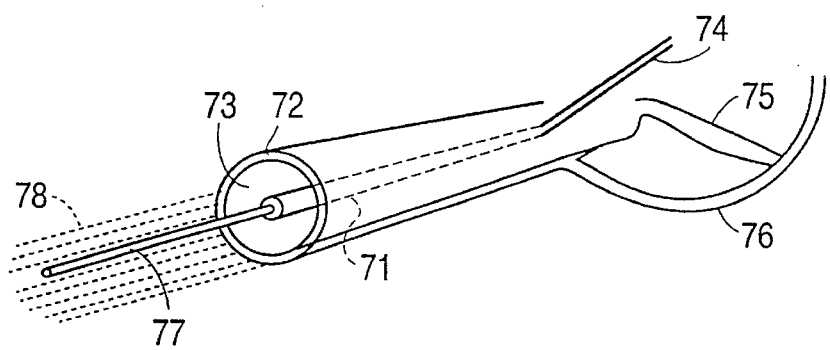
FIG. 5 shows two advantageous developments of the cutting nozzle with an additional suction and irrigation device.

FIG. 5a shows an advantageous arrangement of the instrument holder with the nozzle and an additional suction device and an irrigation device. The nozzle 71 from which the cutting jet 77 emerges is arranged in the center of a suction duct 73 having a circular cross-section. The exit direction of the nozzle extends in parallel to the main axis of the suction duct. The suction in the suction duct is provided by a vacuum generated by an external pump (not shown). The nozzle 71 is electrically insulated from the suction device. The fine droplets which are whirled up by the jet are sucked off by the suction in the suction duct 73.

The outer shell of the suction duct 73 is double-walled so that irrigation can be provided through the interior 72 thereof. The interior 72—in the following called irrigation duct—has a ring-shaped cross-section as shown in the figure. The irrigation liquid 78 which emerges from the irrigation duct acts like a water curtain so that the fine droplets whirled up by the jet 77 are kept down. In addition, the irrigation liquid permits a dilution of the jet solution. By way of the suction duct 73, the irrigation and jet liquid can be sucked off.

Figure 5B:
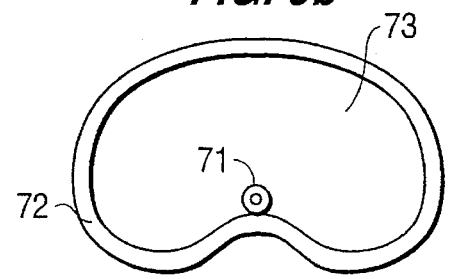

In addition to the instrument holder shown here, other expedient developments are also possible for the cross-section of the suction duct as well as for the arrangement of the nozzle inside the suction duct. A respective example is shown in FIG. 5b. Here, the suction duct 73 has an approximately kidney-shaped cross-section, and the nozzle 71 rests against the wall of the suction duct 73. As in FIG. 5a, the outer shell of the suction duct 73 is double-walled so that the interior 72 forms an irrigation duct.

Figure 6:
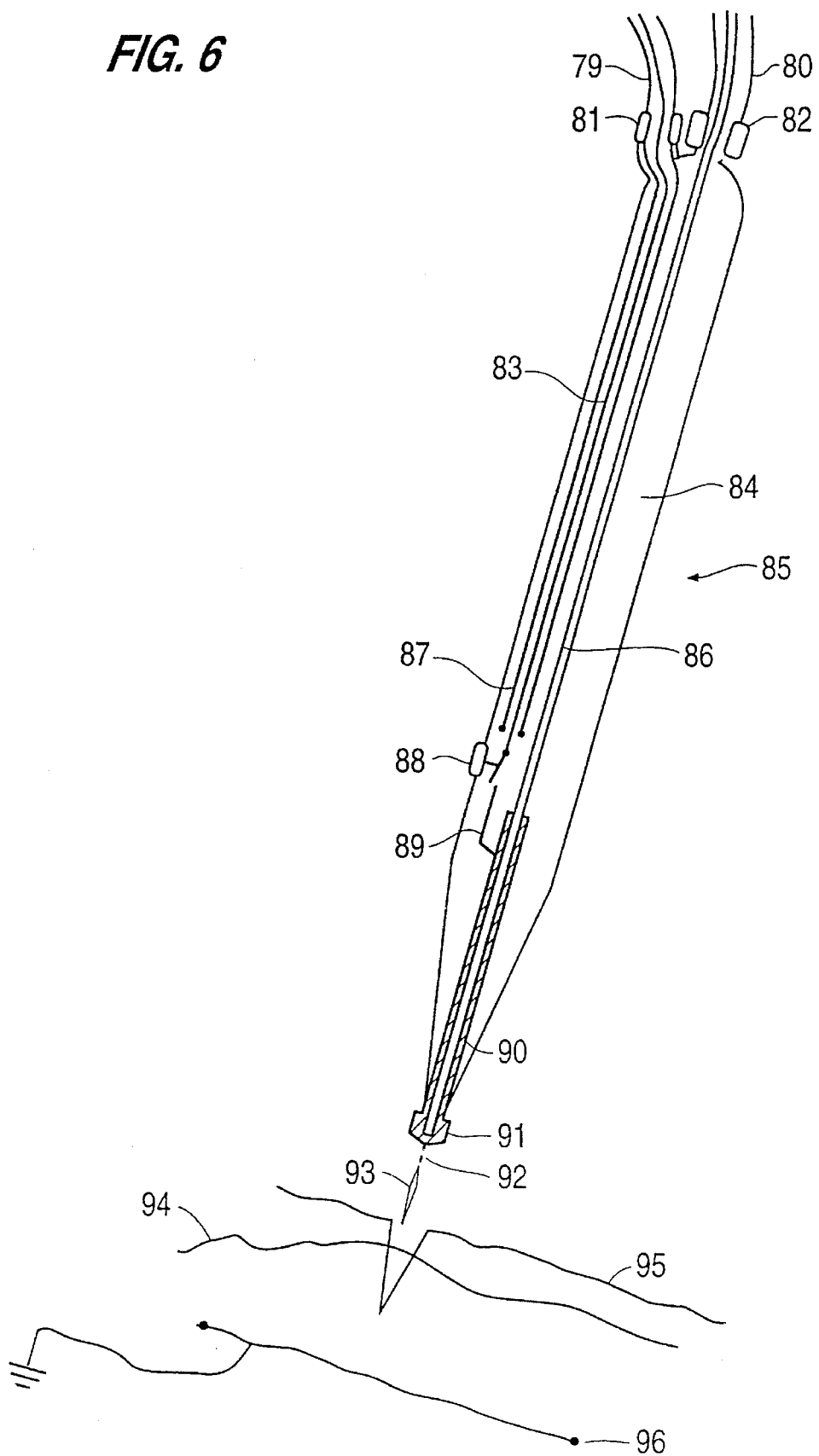
FIG. 6 is a cross-sectional view which shows the details of an embodiment of the instrument holder such as shown schematically in FIGS. 1 through 4.

FIG. 6 illustrates an embodiment of an instrument holder 85 with a nozzle and an HF-supply, but without any suction device or irrigation device. Pressurized cutting liquid is guided to the instrument holder 85 by a pressure hose 80 made of an insulating material. The pressure hose 80 is connected to the instrument holder 85 by a coupling 82. In its central area 84, the instrument holder 85 is also made of an insulating material. A thin duct 86 extends to the front of the nozzle 92 in the interior of instrument holder 85. This duct 86 and the lumen of the pressure hose 80 are dimensioned such that the conducting liquid forms a high electrical resistance, so that the leakage current by way of the conductive liquid column to the pressure generating device becomes negligible.

For cutting liquid supply, the duct then leads into a tube section 90 made of a conductive material. Nozzle 92, which is exchangeable by way of a coupling 91, is disposed at the end of this tube 90. The water jet 93 exits from the nozzle to cut the tissue 95. Blood-conveying vessels 94 in the cutting canal are not cut by the water jet 93, however.

The high frequency electric signal is guided to the instrument holder 85 from a high-frequency generator (not shown), by way of a coaxial cable 79, which is coupled to the instrument holder 85 by a connection 81. In the interior of the instrument holder 85, the high-frequency coaxial conductor extends to the end of the tube section 90. The end of the external conductor 87 of coaxial cable is designed such that a flash-over to the internal conductor 83 is not possible. The internal conductor 83 may be interruptibly connected with the tube section 90 by a switch 88. By pressing or releasing the switch 88, the physician can switch the high frequency on or off.

By way of the tube 90, a high-frequency electric current can flow onto the conductive liquid and, by way of the conductive liquid, can flow to the tissue. As a result of the thermal effect of the high-frequency current, a coagulation takes place in the cutting canal in order to close hemorrhages from the microvessels which were damaged by the water jet. The circuit is closed by way of the neutral electrode 96.

In another advantageous embodiment (not shown in the drawing), the instrument holder comprises a laser as well as a blower or a hot air fan.

For use in minimally invasive surgery, the instrument holder may be miniaturized so that it can be introduced into the body also by way of endoscopic working ducts.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed:

1. In a process used for cutting of organic tissue in which a stream of a cutting liquid is ejected under high pressure from a nozzle to form a cutting jet, the steps of:

providing a cutting liquid which is electrically conductive;

maintaining the cutting liquid electrically and hygienically isolated from a pressure generating system;

applying a high frequency electric signal to the cutting jet; and directing said cutting jet against said organic tissue, thereby simultaneously cutting said organic tissue and transmitting the high frequency electric signal via the cutting jet to the organic tissue during the cutting process to provide high-frequency coagulation.

2. A process according to claim 1, wherein an electric frequency of between 100 and 1,000 kHz having a voltage of above 1,200 volt, is applied to the cutting jet.

3. A process according to claim 1, wherein the nozzle opening has a diameter of from 0.05 to 0.2 mm.

4. A process according to claim 2, wherein the nozzle opening has a diameter of from 0.05 to 0.2 mm.

5. A process according to claim 1, wherein by means of a control circuit, the pressure of the cutting liquid is set to a predetermined working pressure.

6. A process according to claim 4, wherein by means of a control circuit, the pressure of the cutting liquid is set to a predetermined working pressure.

7. A process according to claim 1, wherein by way of a flow rate and pressure measurement, a safety system is controlled which detects nozzle closures and leakages and, if necessary, sets the generating of pressure to zero.

8. A process according to claim 6, wherein by way of a flow rate and pressure measurement, a safety system is controlled which detects nozzle closures and leakages and, if necessary, sets the generating of pressure to zero.

9. A process according to claim 1, wherein the cutting liquid is heated.

* * * * *